United States Patent [19]

Badger et al.

[11] Patent Number: 4,732,898

[45] Date of Patent: Mar. 22, 1988

[54] 2-(2-ARYL-2-OXOALKYLIDENE) ANALOGS OF-3,5-PYRIDINEDICARBOXYLIC ACID DIALKYL ESTERS USEFUL FOR TREATMENT OF CARDIOVASCULAR DISORDERS

[75] Inventors: Edward W. Badger, Dexter; Michael D. Taylor, Ann Arbor, both of Mich.

[73] Assignee: Warner-Lambert Company, Morris Plains, N.J.

[21] Appl. No.: 16,896

[22] Filed: Mar. 3, 1987

Related U.S. Application Data

[63] Continuation-in-part of Ser. No. 857,012, Apr. 29, 1986, abandoned.

[51] Int. Cl.$^4$ .................. A61K 31/455; C07D 211/90; C07D 401/06; C07D 215/54
[52] U.S. Cl. .................................... 514/225; 514/226; 514/233; 514/236; 514/248; 514/249; 514/252; 514/256; 514/259; 514/300; 514/307; 514/314; 514/332; 514/333; 514/337; 514/338; 514/339; 514/340; 514/341; 514/342; 514/343; 514/344; 514/352; 514/355; 514/356; 514/312; 544/49; 544/50; 544/52; 544/54; 544/58.6; 544/96; 544/98; 544/235; 544/238; 544/284; 544/333; 544/353; 544/405; 546/121; 546/122; 546/145; 546/146; 546/147; 546/168; 546/170; 546/256; 546/262; 546/263; 546/269; 546/270; 546/271; 546/273; 546/274; 546/275; 546/278; 546/279; 546/280; 546/281; 546/283; 546/284; 546/286; 546/310; 546/315; 546/321; 546/322; 546/156

[58] Field of Search ............... 546/262, 263, 286, 310, 546/321, 322, 315, 121, 122, 145, 146, 147, 156, 168, 170, 256, 269, 276, 271, 273, 274, 275, 278, 279, 280, 281, 283, 284; 514/332, 344, 352, 355, 356, 225, 226, 233, 236, 248, 249, 252, 256, 259, 300, 307, 314, 333, 337, 338, 339, 340, 341, 342, 343, 312; 544/49, 50, 52, 54, 58.6, 96, 98, 235, 238, 284, 333, 353, 405

[56] References Cited

U.S. PATENT DOCUMENTS 4,146,627 3/1979 Wehinger et al. .................. 546/278

FOREIGN PATENT DOCUMENTS

| | | |
|---|---|---|
| 803474 | 2/1974 | Belgium . |
| 804160 | 2/1974 | Belgium . |
| 817540 | 1/1975 | Belgium . |
| 843576 | 12/1976 | Belgium . |
| 861964 | 6/1978 | Belgium . |
| 893984 | 1/1983 | Belgium . |
| 2248150 | 4/1974 | Fed. Rep. of Germany . |
| 3239273A | 4/1984 | Fed. Rep. of Germany . |
| 1389509 | 4/1975 | United Kingdom . |

Primary Examiner—Henry R. Jiles
Assistant Examiner—Dale A. Bjorkman
Attorney, Agent, or Firm—Joan Thierstein

[57] ABSTRACT

The present invention are 2-(2-aryl-2-oxo-alkylidene) analogs of 1,2,3,4-tetrahydropyridine-3,5-pyridinecarboxylic acids and particularly esters thereof having valuable calcium antagonist and positive inotropic activity useful in the treatment of cardiovascular disorders, pharmaceutical compositions and methods of use therefor.

20 Claims, No Drawings

2-(2-ARYL-2-OXOALKYLIDENE) ANALOGS OF-3,5-PYRIDINEDICARBOXYLIC ACID DIALKYL ESTERS USEFUL FOR TREATMENT OF CARDIOVASCULAR DISORDERS

This is a continuation-in-part of U.S. application Ser. No. 06/857,012 filed Apr. 29, 1986, abandoned.

BACKGROUND OF THE INVENTION

The present invention is for novel analogs of 2-(2-aryl-2-oxoalkylidene)-1,2,3,4-tetrahydropyridine polyesters having valuable calcium antagonist and cardiotonic properties useful in the treatment of cardiovascular disorders, pharmaceutical compositions and methods of use therefor.

Dihydropyridine polyesters have been described in the literature as useful for treating various cardiovascular diseases. However, the first description of 2-alkylidene derivatives of 1,2,3,4-tetrahydropyridine-3,5-pyridine dicarboxylic acid dialkyl esters is found in copending application U.S. Ser. No. 677,150 filed Nov. 30, 1984. Thus, references of the copending application are also related to the analogs of the present invention and, therefore, U.S. application Ser. No. 677,150 is incorporated by reference herein.

SUMMARY OF THE INVENTION

Accordingly the present invention is a compound of the formula (I)

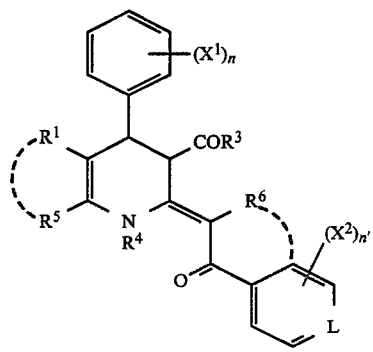

and pharmaceutically acceptable base or acid addition salts thereof; wherein
(1) ---- is nothing or a bond;
(2) $R^1$ is
   (i) cyano,
   (ii) nitro,
   (iii)

wherein $R^2$ is (i) $OR^7$ is hydrogen or wherein $ZR^8$ is alkylenyl of from one to six carbons, inclusive, and $R^8$ is hydrogen, aryl, heteroaryl, amino, monoalkylamino wherein the alkyl is of from one to six carbons, inclusive, or dialkylamino wherein alkyl is of from one to six carbons, inclusive; or
   (iv) A-$(CH_2)_q$ wherein q is an integer of two, three, or four and A is

when taken together with $R^5$;
(3) $R^3$ is
   (i) $ZR^8$ wherein Z and $R^8$ are each independently as defined above,
   (ii) $OR^7$ wherein $R^7$ is independently as defined above, or
   (iii) phenyl unsubstituted or substituted by from one to five, preferably one to three substituents wherein the substituents are the same or different and are (i) hydrogen, (ii) alkyl of from one to six carbons, inclusive, (iii) nitro, halogen, (iv) alkoxy of from one to six carbons, inclusive, (v) cyano, (vi) amino, (vii) monoalkylamino wherein the alkyl is of from one to six carbons, inclusive, (viii) dialkylamino wherein the alkyl is of from one to six carbons, inclusive, or (ix) trifluoromethyl;
(4) $R^4$ is hydrogen or alkyl of from one to six carbons, inclusive;
(5) $R^5$ is
   (i) hydrogen,
   (ii) alkyl of from one to six carbons, inclusive, or
   (iii) taken together with $R^1$ as defined above;
(6) $R^6$ is
   (i) hydrogen,
   (ii) alkyl of from one to six carbons, inclusive, or
   (iii) $(CH_2)_{q'}$ when taken together with $X^2$ when $X^2$ is on the carbon having the ---- and q' is 1, 2, or 3, preferably 2;
(7) n is an integer of zero through five, preferably one and two;
(8) $X^1$ may each be the same or different and is
   (i) alkyl of from one to six carbons, inclusive,
   (ii) nitro,
   (iii) halogen,
   (iv) alkoxy of from one to six carbons, inclusive,
   (v) cyano,
   (vi) amino,
   (vii) monoalkylamino wherein the alkyl is of from one to six carbons, inclusive,
   (viii) dialkylamino wherein the alkyl is of from one to six carbons, inclusive, or
   (ix) trifluoromethyl; and
(9) $X^2$ may each be the same or different and is
   (i) alkyl of from one to six carbons, inclusive,
   (ii) nitro,
   (iii) halogen,
   (iv) alkoxy of from one to six carbons, inclusive,
   (v) cyano,
   (vi) amino,
   (vii) monoalkylamino wherein the alkyl is of from one to six carbons, inclusive,
   (viii) dialkylamino wherein the alkyl is of from one to six, inclusive, or
   (ix) trifluoromethyl;
(10) n' is an integer of from 0-5, preferably 0-2; 11) L is CH; or N with the proviso that n' is 0 and ---is nothing.

The present invention also relates to a pharmaceutical composition for the treatment of cardiovascular disorders comprising an amount effective for the treatment of the cardiovascular disorders of the compound of formula I as defined above and a pharmaceutically acceptable carrier.

Additionally, the present invention is a method of treating cardiovascular disorders in a mammal suffering therefrom, which comprises administering such mammals a compound of the formula I above.

Finally, the present invention also includes a process for preparing the compound of formula I as defined above.

The specific cardiovascular disorders contemplated above include congestive heart failure, myocardial ischemia, angina, hypertension, and the like.

DETAILED DESCRIPTION OF THE INVENTION

The meaning of terms as used in the present invention is as follows:

Alkyl of from one to six carbons inclusive as methyl, ethyl, propyl, butyl, pentyl, hexyl and isomers thereof.

Alkylenyl of from one to six carbons, inclusive, is methylenyl, ethylenyl, propylenyl, butylenyl, pentylenyl, hexylenyl and isomers thereof.

Aryl is optionally substituted phenyl which may have one or two substituents which may be the same or different and are selected from a group consisting of alkyl of from one to six carbons, inclusive, $NO_2$, halogen, alkoxy, amino, monoalkylamino wherein the alkyl is of from one to six carbons, inclusive, and dialkylamino wherein the alkyl is of from one to six carbons, inclusive.

Alkoxy of from one to six carbons, inclusive, includes a straight or branched chain alkoxy, such as, methoxy, ethoxy, propoxy, butoxy, pentoxy, hexoxy and isomers thereof.

Halogen is fluoro, chloro, bromo or iodo, preferably fluoro, chloro, or bromo.

Heteroaryl means thienyl, furyl, pyryl, pyridyl, quinolyl, isoquinolyl, pyrimidyl, pyridazinyl, quinazolyl, quinoxalyl, pyrazolyl, imidazolyl, orazolyl, isoxazolyl, thiazolyl, triazolyl, pyrazinyl, oxazinyl, thiazinyl, indolizinyl, indolyl, benzofuranyl, indazolyl, benzothienyl, benzimidazolyl, benzoxazolyl, cinnolinyl, phthalazinyl, naphthyridinyl or benzothiazinyl. No limitation is meant as to the location of the bond by which the heteroaryl is attached and such a bond location is within the skill of the ordinary artisan.

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxices, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; -N-methyl-glucosamine; N-methylpiperazine; morpholine; ethylenediamine; N-benzylphenethylamine; tris(hydroxymethyl)-aminomethane; and the like. (See for example, "Pharmaceutical Salts," *J. Pharm. Sci.*, 66(1):1–19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The base salts of compounds of formula I described above are prepared by reacting the appropriate base with a stoichiometric equivalent of the acid compounds of formula I to obtain pharmacologically acceptable base salts thereof.

The acid solution salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may also exist in hydrated or solvated forms.

The preferred compounds of the present invention are of formula I wherein $R^1$ is $COOR^2$.

The more preferred compounds of the present invention include (2Z,3α,4β)-(I)-diethyl-1,2,3,4-tetrahydro-6-methyl-2-[2-oxo-2-(4-pyridinyl) ethylidene]-4-[2-(trifluoromethyl)phenyl-3,5-pyridinedicarboxylate and (2Z,3α,4β)-diethyl-2-[2-(4-chlorophenyl) -2-oxoethylidene]-1,2,3,4-tetrahydro-6-methyl-4-[2-trifluoromethyl)phenyl]-3,5-pyridine-dicarboxylate.

Generally, the compounds of formula I may be conveniently synthesized by a process analogous to Hantzsch dihydropyridine synthesis as described in Ann., Vol. 215, 1, 72 (1882), and Ber. 18, 1744 (1885). The synthesis is shown in the following Schemes I and II.

Scheme I

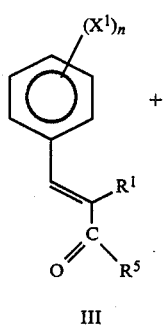

III

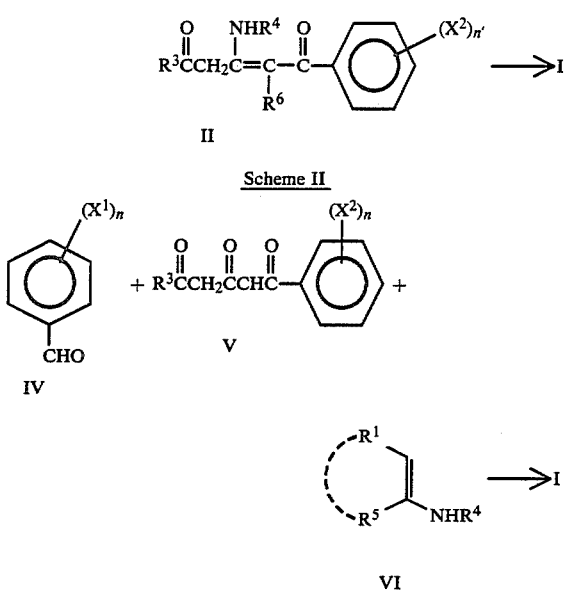

The compounds of formula II, III, IV, V, and VI wherein $R^1$, $R^3$, $R^4$, $R^5$, $R^6$, $X^1$, $X^2$, n and n' are as defined above. The conditions of Schemes I or II reactions may include a solvent such as methanol, ethanol, isopropanol methoxyethanol, ethoxyethanol or the like, preferably ethanol and further preferably using equivalent amounts of reactants. Each reaction is preferably at reflux temperature for from one to sixty hours, preferably from ten to twenty-four hours, under anhydrous conditions.

The products of the reactions described herein are isolated by conventional means such as extraction, distillation, chromatography, and the like.

The starting materials of formula II, III, IV, V or VI are commercially available or can be readily synthesized by known methods or methods analogous to those known in the art.

The compounds of the invention may contain an asymmetric carbon atom. Thus, the invention includes the individual stereoisomers, and the mixtures thereof. The individual isomers may be prepared or isolated by methods known in the art.

The compounds of formula I are found to possess activity as calcium channel blockers and also to possess a direct positive inotropic activity. Thus, the compounds of formula I are useful for the treatment of congestive heart failure, coronary heart disease, myocardial ischemia, angina, and hypertension. Particularly, the compounds of the present invention are superior agents for the treatment of congestive heart failure. That is, in generally accepted tests, the compounds of the present invention produce substantial increases in contractility and decreases in blood pressure, without affecting heart rate. Thus, biological effects of the present invention compounds include beneficial effects similar to those observed for calcium antagonists. Additionally, the effects include a complementary direct stimulatory effect on the myocardium as also observed in a generally accepted test in isolated atrial tissue. Particularly, initial direct stimulation by the compounds of the present invention provides additional support to a failing heart complementary to afterload reduction resulting from vasodilation. Such stimulation is also known as a positive inotropic effect.

The usefulness of the compounds of formula I of the present invention as generally described above is demonstrated by effects on myocardial contractility, heart rate and coronary flow in the following test procedures.

TEST FOR INOTROPIC, CHRONOTROPIC, AND VASCULAR ACTIVITIES IN THE ISOLATED LANGENDORFF RAT HEART PREPARATION (CARDIOVASCULAR ISOLATED HEART - CVIH)

Perfusion Technique

Male rats (400–600 gms) are pretreated with 2000 units Na heparin (Parke-Davis) and anesthetized with Na pentobarbital (50 mg/kg, Butler Co.) administered intraperitoneally. Once anesthetized, the rat heart is rapidly excised, the ascending aorta fitted to the aorta perfusion cannula, and secured with a ligature. The coronary arteries are perfused initially at a rate of about 15 ml/min for two to three minutes, after which they are perfused at constant pressure of 70 mm Hg and temperature of 37° C. The electrocardiogram (ECG) is recorded using two platinum electrodes positioned at the base and apex of the left ventricle (LV). The LV is instrumented via the mitral valve with a 4F Millar catheter tip pressure transducer. The catheter is advanced to the apex then withdrawn slightly. Once properly positioned, the catheter is anchored to the perfusion cannulae with an alligator clip. A second heart is excised, cannulated, and perfused by the same method outlined above. Both hearts are tested in parallel. The standard physiological salt solution (PSS) is a modified Krebs Henseleit bicarbonate buffer of the following composition in mM concentration: NaCl, 127; $NaHCO^3$, 25; dextrose, 5.5; Na Pyruvate, 2.0; KCl, 4.7; $MgSO^4$, 1.1; $KH_2PO^4$, 1.2; $CaCl^2 \cdot 2H^2$, 2.5; $CaNa^2$ EDTA, 0.05.

A 30-minute stabilization period is observed before starting the test protocol.

Microprocessor Controlled Coronary Perfusion and Drug Delivery System

A microprocessor control system is used as a servo mechanism which permits coronary perfusion pressure (CPP) and drug concentration to be maintained constant independent of changes in coronary flow. The level at which CPP and drug concentration are maintained can be changed by commands communicated through the microprocessor keyboard. Dose-response curves are carried out by perfusing concentrated drug solution (DC) at rates proportional to total coronary flow ($CF_T$). Drug concentrations are increased by proportionate increases in the rate of DC infusion over $CF_T$ via the microprocessor keyboard. The proportional flow rates for DC:$CF_T$ are about 0.00005:1 at the low end and 0.0015:1 at the high end of the dose response curve.

Dose-response curves encompassing at least two log units are carried out in one-half log increments starting at a subthreshold dose and ending at a dose which produces near maximal response.

Measurements

Measurements for CVIH are maximum positive first derivative of LVP (LV+dP/dt$_{max}$), heart rate (HR), and coronary flow (CF). Units are: LV+dP/dt$_{max}$, millimeter of mercury/second (mm Hg/sec); HR, beats/minute (bpm) and CF, milliliters/minute (ml/min). LV+dP/dt$_{max}$ is derived from the LVP signal by a differential amplifier and recorded. HR is calculated from the ECG strip chart recording and CF is calculated by recording analog outputs from pumps 1 and 2. Outputs from pump #1 =CF$_T$ and the output from pump #2 =CF for heart B (CF$_B$). CF for heart A (CF$_A$) is calculated (CF$_T$=CF$_B$=CF$_A$). All pumps are calibrated weekly or when pump tubing is replaced.

Compounds are solubilized in DMSO and diluted with water when possible. EC$^{25}$ data are obtained from data that is digitized and averaged in a conventional manner.

Results from the above tests using compounds of the noted examples described hereinafter are shown in Table I as follows:

TABLE I

| Ex. No. | EC$_{25}$ Flow | EC$_{25}$ Contractility | IC$_{50}$* |
|---------|----------------|--------------------------|------------|
| 1 | 0.3 μM | 0.1 μM | 280 nM |
| 2 | <.1 | >3 | 20 |
| 3 | <.1 | <0.1 | 190 |
| 4 | 0.3 | >3 | 52 |
| 5 | 0.13 | >3 | 360 |
| 6 | 0.2 | >3 | — |
| 7 | 0.1 | >3 | 130 |
| 8 | 0.3 | >3 | >1000 |
| 9 | 0.4 | 1.2 | 110 |
| 10 | 1.4 | 2.0 | >1000 |
| 11 | 1.0 | 1.0 (EC$_{20}$) | >1000 |
| 12 | not yet tested | | >1000 |
| 13 | 1.0 | 1.0 | 39 |
| 14 | 1.0 | 1.0 | 85 |
| 15 | 1.0 | 1.0 | 180 |
| 16 | 1.0 | 1.0 | 25 |

*Index of dihydropyridine receptor affinity: IC$_{50}$ for inhibition of [$^3$H]—nitrendipine binding in rat brain homogenate.

TEST FOR IN VIVO MYOCARDIAL INOTROPIC ACTIVITY IN THE ANESTHETIZED DOG

Method

Adult mongrel dogs of either sex are anesthetized with pentobarbital, 35 mg/kg, IV, and are maintained under anesthesia with a continuous infusion of pentobarbital, 3.5 mg/kg/hr. The trachea is intubated, but the animals are permitted to breathe spontaneously. A cannula is inserted into the femoral vein for administering test agents. A Millar catheter tip pressure transducer or a fluid filled catheter is inserted into the ascending aorta via the femoral artery for measuring pressure. A Millar catheter tip pressure transducer is passed into the left ventricle via the left carotid artery for measuring left ventricular blood pressure. Needle electrodes are placed subcutaneously for recording a lead II electrocardiogram. Before administering test agents, control data is acquired over a period of at least thirty minutes.

The test agent is dissolved in dimethylacetamide. Each dose is administered in a volume of 0.5 ml over a period of one minute. Appropriate vehicle controls are also administered.

When tested by this protocol, the compound of the following Example 2, when administered at a dose of 1 mg/kg, produced an increase in contractility of 99%, a decrease in blood pressure of 21%, and an increase in heart rate of 67%.

Accordingly, the present invention also includes a pharmaceutical composition for treating cardiovascular disorders comprising an effective amount for use in cardiovascular disorders of a compound of formula I as defined above and a pharmaceutically acceptable carrier in an appropriate unit dosage form.

Also the present invention thus also includes a method for treating cardiovascular disorders comprising administering to mammals, including humans, suffering therefrom either orally or parenterally the corresponding pharmaceutical composition of the compound of formula I.

A physician or veterinarian of ordinary skill readily determines a subject exhibiting symptoms of the diseases. The routes of administration and the dosage forms therefore are from among those conventional to the pharmaceutical art. Regardless of the route of administration selected the invention provides a compound of formula I, in unit dosage form comprising the compound either alone or in admixture with a pharmaceutically acceptable carrier appropriately selected from those known.

An effective but nontoxic quantity of the compound I is employed in treatment. The dosage regimen is selected in accordance with a variety of factors including the type, age, weight, sex, and medical condition of the mammal, the severity of symptoms of the disease being treated, the route of administration and particular compound of formula I employed. An ordinarily skilled physician or veterinarian will readily determine and prescribe the effective amount of the compound I to prevent or arrest the progress of the disease condition. In so proceeding, the physician or veterinarian could employ relatively low dosages at first, subsequently increasing the dose until a maximum response is obtained. For convenience, the total daily dosage may be divided and administered in portions during the day if desired.

Initial dosages of the compounds of the invention are ordinarily in the area of 0.1 mg/kg up to at least 1 mg/kg per dose IV, preferably to 0.1–0.3 mg/kg IV and are given as needed. When other forms of administration are employed equivalent doses are administered.

It is understood that the compositions and methods of treatment of the present invention as described above also include the free acid, the pharmacologically acceptable base salts and acid addition salts of the compounds of formula I.

The following examples further illustrate the invention, but are not meant to be limiting thereto.

EXAMPLE 1

(2Z,3α,4β)-(±)-Diethyl-1,2,3,4-tetrahydro-6-methyl-2-(2-oxo-2-phenylethylidene)-4-[2-(trifluoromethyl)-phenyl]-3,5-pyridinedicarboxylate.

A solution of ethyl 5-phenyl-3,5-dioxopentanoate (2.88 g, 12.3 mMol), 2-(trifluoromethyl)benzaldehyde (2.14 g, 12.3 mMol), and ethyl 3-aminocrotonate (1.6 g, 12.3 mMol) in ethanol (50 ml) is boiled under reflux for 18 hours and evaporated to a yellow oil. this oil is then separated on a 51×450 mm Michel-Miller double-taper high performance medium-pressure liquid chromatography (MPLC) system, eluting with dichloromethane/ethyl acetate 98/2, collecting 20 ml fractions. The product appears in fractions 26–35 after the solvent front. These fractions are combined and evaporated to a yellow oil, which is recrystallized from 2,2,4-trimethylpentane to yield 0.48 g (8%), mp 111–112.

IR: 3000, 1740, 1692, 1643 cm$^{-1}$; NMR (200 MHz, CDCl$_3$)δ11.90 (s, 1H), 7.87-7.11 (m, 9H), 5.89 (s, 1H), 5.06 (s, 1H), 4.22 (d of q, J=7.1, 2.56 Hz, 2H), 4.03 (q,

J=7.26 Hz, 2H), 3.42 (s, 1H), 2.61 (s, 3H), 1.27 (t, J=7.1 Hz, 3H), 1.09 (t, J=7.2 Hz, 3H); MS: m/z (int); 501 (7) [MI], 456 (4.4), 428 (88.4), 400 (3.9), 382 (11.1), 356 (10), 105 (100), 77 (41.1).

| Microanalysis: | C | H | N | F |
|---|---|---|---|---|
| Calculated | 64.67 | 5.23 | 2.79 | 11.37 |
| Found | 64.87 | 5.53 | 3.03 | 11.08 |

EXAMPLE 2

(2Z,3α,4β)-(±)-Diethyl-1,2,3,4-tetrahydro-6-methyl-2-[2-oxo-2-(4-pyridinyl)ethylidene]-4-[2-(trifluoroethyl)-phenyl]-3,5-pyridinedicarboxylate.

As for Example 1, ethyl 5-(4-pyridyl)-3,5-dioxopentanoate, 2-(trifluoromethyl)benzaldehyde, and ethyl 3-aminocrotonate produced a bright yellow solid. mp 128-128.5; yield 2.3%. IR: 3000, 1740, 1701, 1623 cm$^{-1}$; NMR (300 MHz, CDCl$_3$) δ 11.89 (s, 1H), 8.72 (d, J=5.8 Hz, 2H), 7.71-7.64 (m, 3H), 7.44-7.30 (m, 2H), 7.10 (d, J=7.6 Hz, 1H), 5.82 (s, 1H), 5.08 (s, 1H), 4.23 (d of q, J=1.26, 6.7 Hz, 2H), 4.04 (d of q, J=7.7, 4.1 Hz, 2H), 3.45 (s, 1H), 2.61 (s, 3H), 1.28 (t, J=7.0 Hz, 3H), 1.09 (t, J=7.0 Hz, 3H); MS m/z (int): 503 (30.2) [M+1], 457 (7.7), 429 (100), 383 (11.5), 106 (46.4).

| Microanalysis: | C | H | N | F |
|---|---|---|---|---|
| Calculated | 62.15 | 5.02 | 5.58 | 11.34 |
| Found | 62.08 | 5.16 | 5.36 | 11.29 |

EXAMPLE 3

(2Z,3α,4β)-Diethyl-2-[2-(4-chlorophenyl)-2-oxoethylidene]-1,2,3,4-tetrahydro-6-methyl-4-[2-(trifluoromethyl)phenyl]-3,5-pyridinedicarboxylate.

As for Example 1, ethyl 5-(4-chlorophenyl)-3,5-dioxopentanoate, 2-(trifluoromethyl)benzaldehyde, and ethyl 3-aminocrotonate produced a bright yellow solid. mp 129-130; yield 8%. IR: 2984, 1738, 1689, 1622 cm$^{-1}$; NMR (200 MHz, CDCl$_3$) 11.87 (s, 1H), 7.81-7.68 (m, 3H), 7.45-7.30 (m, 4H), 7.11 (d, J=7.7 Hz, 1H), 5.82 (s, 1H), 5.06 (s, 1H), 4.22 (d of q, J=7.1, 2.7 Hz, 2H), 4.03 (d of q, J=7.3, 3.3 Hz, 2H), 3.42 (s, 1H), 2.60 (s, 3H), 1.27 (t, J=7.1 Hz, 3H), 1.09 (t, J=7.2 Hz, 3H); Ms m/z (int): 535 (7.6) [MI], 490 (4.3), 462 (100), 390 (9), 139 (30.1).

| Microanalysis: | C | H | N | F | Cl |
|---|---|---|---|---|---|
| Calculated | 60.51 | 4.70 | 2.61 | 10.63 | 6.62 |
| Found | 60.51 | 4.91 | 2.80 | 10.67 | 6.73 |

EXAMPLE 4

(2Z,3α,4β)-Diethyl-2-[2-(4-fluorophenyl)-2-oxoethylidene]-1,2,3,4-tetrahydro-6-methyl-4-[2-(trifluoromethyl)phenyl]-3,5-pyridinedicarboxylate.

As for Example 1, ethyl 5-(4-fluorophenyl)-3,5-dioxopentanoate, 2-(trifluoromethyl)benzaldehyde, and ethyl 3-aminocrotonate produced a yellow solid. mp 111.5-112; yield 12%. IR: 2987, 1741, 1701, 1624 cm$^{-1}$; NMR (200 MHz, CDCl$_3$)δ6 11.86 (s, 1H), 7.91-7.84 (m, 2H), 7.72 (d of d, J=7.15, 0.76, 1H), 7.45-7.32 (m, 2H), 7.13-7.04 (m, 3H), 5.83 (s, 1H), 5.06 (s, 1H), 4.23 (d of q, J=7.1, 2.6 Hz, 2H), 4.03 (d of q, J=7.3, 0.9 Hz, 2H), 3.41 (s, 1H), 2.60 (s, 3H), 1.27 (s, J=7.1, 3H), 1.09 (t, J=7.2, 3H); MS m/z (int): 519 (5.9) [MI], 474 (4.5), 446 (100), 400 (11.8), 374 (8.2), 123 (23.9).

| Microanalysis: | C | H | N | F |
|---|---|---|---|---|
| Calculated | 62.43 | 4.85 | 2.70 | 14.63 |
| Found | 62.42 | 4.87 | 2.68 | 14.82 |

EXAMPLE 5

(2Z,3α,4β)-Diethyl-2-[2-(4-methylphenyl)-2-oxoethylidene]-1,2,3,4-tetrahydro-6-methyl-4-[2-(trifluoromethyl)phenyl]-3,5-pyridinedicarboxylate.

As for Example 1, ethyl 5-(4-methylphenyl)-3,5dioxopentanoate, 2-(trifluoromethyl)benzaldehyde, and ethyl 3-aminocrotonate produced a yellow solid. mp 85-87; yield 4%. IR: 2989, 1745, 1709, 1622 cm$^{-1}$; NMR (200 MHz, CDCl$_3$) δ11.91 (s, 1H), 7.84-7.68 (m, 3H), 7.52-7.11 (m, 4H), 5.88 (s, 1H), 5.05 (s, 1H), 4.22 (d of q, J=7.2, 2.5 Hz, 2H), 4.04 (d of q, J=8.0, 3.5 Hz, 2H), 3.41 (s, 1H), 2.61 (s, 3H), 2.39 (s, 3H), 1.27 (t, J=7.2 Hz, 3H), 1.09 (t, J=7.2 Hz, 3H); MS (FAB, thioglycerol) m/z (int): 516 (35.5) [M+1], 470 (100), 442 (65.3), 370 (17.7).

| Microanalysis: | C | H | N | F |
|---|---|---|---|---|
| Calculated | 65.24 | 5.48 | 2.72 | 11.06 |
| Found | 65.16 | 5.42 | 2.43 | 11.37 |

EXAMPLE 6

(2Z,3α,4β)-(±)-Diethyl-1,2,3,4-tetrahydro-6-methyl-2-[2-oxo-2-4-(dimethylamino)phenyl)ethylidene]-4-[2-(trifluoromethyl)phenyl]-3,5-pyridine-dicarboxylate.

As for Example 1, ethyl 5-(4-dimethylamino-phenyl)-3,5-dioxopentanoate, 2-(trifluoromethyl) benzaldehyde, and ethyl 3-aminocrotonate produced a yellow solid. Recrystallized from isopropyl ether. Yellow crystals, 8% yield. IR: 3000, 1737, 1735, 1700, 1642 cm$^{-1}$; NMR (200 MHz, CDCl$_3$)δ11.96 (s, 1H), 7.80 (d, J=9.0 Hz, 1H), 7.68 (d, J=7.3 Hz, 1H), 7.39-7.27 (m, 2H), 7.13 (d, J=7.3 Hz, 1H), 6.63 (d, J=9.0 Hz, 1H), 5.85 (s, 1H), 5.03 (s, 1H), 4.21 (d of q, J =2.1, 7.1 Hz, 2H), 4.02 (d of q, J=2.0, 7.4 Hz, 2H), 3.38 (s, 1H), 3.04 (s, 6H), 2.59 (s, 3H), 1.26 (d of t, J=0.8, 6.9 Hz, 3H), 1.12 (t, J=6.0 Hz, 3H); MS [FAB/thioglycerol m/z (int): 545 [M+1](100), 499 (34), 471 (21.9), 424 (10.4), 399 (26.5), 332 (12.4).

| Microanalysis: | C | H | N | F |
|---|---|---|---|---|
| Calculated | 63.96 | 5.74 | 5.14 | 10.47 |
| Found | 63.66 | 5.77 | 4.89 | 10.62 |

EXAMPLE 7

(2Z,3α,4β)-(±)-1,2,3,4-Tetrahydro-6-methyl-5-nitro-2-[2-oxo-2-phenylethylidene]-4-[2-(trifluoromethyl) phenyl]-3-pyridinedicarboxylic acid ethyl ester.

A mixture of 1-(2-trifluoromethyl)-2-nitro-buten-3-one (4.3 g) and 5-phenyl-3-amino-5-oxo-2pentanoate (3.8 g) were combined and heated at reflux for 16 hours. After evaporation of the solvent, the residue was purified by medium pressure liquid chromatography (1:1, ethyl acetate:hexane) to give a bright yellow glass, 0.1 g. IR: 1737, 1639; NMR (CDCl$_3$, 200 MHz) δ12.04 (2, 1H), 7.89–7.03 (m, 9H), 6.09 (s, 1H), 5.36 (s, 1H), 4.29–4.18 (m, 2H), 3.55 (s, 1H), 2.78 (s, 3H), 1.28 (t, J=6.9 Hz, 3H).

| Microanalysis: | C | H | N |
|---|---|---|---|
| Calculated | 60.76 | 4.46 | 5.90 |
| Found | 60.46 | 4.48 | 5.77 |

EXAMPLE 8

[trans-(Z)]-2-[3-Benzoyl-3,4-dihydro-6-methyl-5-nitro-4-[2-(trifluoromethyl)phenyl]-2-(1H)pyridinylidene]1-phenylethanone.

A mixture of 1-(2-trifluoromethyl)-2-nitro-buten-3-one (1.8 g) and 1,5-diphenyl-3-amino-1,5-dioxo-2-pentene (1.8 g) were combined and heated at reflux for 30 hours. After evaporation of the solvent, the residue was purified by medium pressure liquid chromatography (1:1, ethyl acetate:hexane) to give a bright yellow glass, 0.15 g (4%). IR: 1686, 1631; NMR (CDCl$_3$, 200 MHz) δ12.1 (s, 1H), 7.96–7.15 (m, 14H), 5.99 (s, 1H), 5.14 (s, 1H), 4.56 (s, 1H), 2.83 (s, 3H); MS 506 (M+1), 489 (5), 401 (20), 105 (100).

| Microanalysis: | C | H | N |
|---|---|---|---|
| Calculated | 60.40 | 4.18 | 5.53 |
| Found | 60.08 | 4.48 | 5.36 |

(4α,5β,6Z)-(±)-Ethyl-5-benzoyl-1,4,5,6-tetrahydro-2-methyl-6-(2-oxo-2-phenylethylidene)-4-[2-trifluoromethyl)phenyl]3-pyridinecarboxylate.

As for Example 1, 1,5-diphenyl-1,3,5-trioxopentane, 2-(trifluoromethyl)benzaldehyde, and ethyl 3-aminocrotonate produced a light yellow solid. Yield 0.55 g, 6%, mp 187–188. IR: 3441, 1723, 1676 cm$^{-1}$; NMR (200 MHz, DMSO)δ10.45 (d, J=5.0 Hz, 1H), 7.99 (d, J=6.8 Hz, 2H), 7.89 (d, J=4.7 Hz, 1H), 7.68–7.61 (m, 6H), 7.57–7.25 (m, 4H), 6.86 (m, 2H), 4.62 (s, 1H), 4.25 (q, J=7.2 Hz, 2H), 3.19 (d, J=1.3 Hz, 1H), 1.47 (s, 3H), 1.26 (t, J=7.1 Hz, 3H); MS m/z (int): 533 (16.8) [M+1], 504 (1.3), 487 (1.3), 460 (63.6), 388 (2.8), 105 (58.2), 44 (100).

| Microanalysis: | C | H | N | F |
|---|---|---|---|---|
| Calculated | 69.91 | 4.73 | 2.63 | 10.70 |
| Found | 69.59 | 5.02 | 2.73 | 10.79 |

EXAMPLE 10

(2Z,3α,4β)-Ethyl-1,2,3,4,5,6,7,8-octahydro-5-oxo-2-(2-oxo-2-phenylethylidene)-4-[2-trifluoromethyl)phenyl]-3-quinolinecarboxylate.

As for Example 1, ethyl 3,5-dioxo-5-phenyl pentanoate, 2-(trifluoromethyl)benzaldehyde, and 3-amino-2-cyclohexen-1-one produced a bright yellow solid. Yield 6.2%, mp 205-206. IR: 3000, 1726, 1658, 1641, 1624 cm$^{-1}$; NMR (200 MHz, CDCl$_3$)δ11.95 (s, 1H), 7.87 (d of d, J=6.8, 1.7 Hz, 2H), 7.67 (d of d, J=7.4, 1.7 Hz, 1H), 7.56–7.25 (m, 5H), 7.02 (d, J=7.2 Hz, 1H), 5.99 (s, 1H), 5.03 (s, 1H), 4.19 (d of q, J=7.1, 1.5 Hz, 2H), 3.47 (s, 1H), 2.78–2.70 (m, 2H), 2.45–2.39 (m, 2H), 2.19–2.08 (m, 2H), 1.27 (t, J=7.1 Hz, 3H); MS m/z (int): 483 (6.4) [MI], 410 (100), 390 (19.2), 338 (9.4), 322 (1.6), 292 (4.6), 264 (7.9), 236 (4.0), 105 (54.7).

| Microanalysis: | C | H | N | F |
|---|---|---|---|---|
| Calculated | 67.07 | 5.00 | 2.90 | 11.79 |
| Found | 67.09 | 5.29 | 3.11 | 11.83 |

EXAMPLE 11

(2Z,3α,4β)-Ethyl-5-cyano-2-(3,4-dihydro-1-oxo-2-(1H)-naphthalenylidene)-1,2,3,4-tetrahydro-6-methyl-4-[2-trifluoromethyl)phenyl]-3-pyridinecarboxylate.

As for Example 1, ethyl 1,2,3,4-tetrahydro-1-oxonaphthalene-2-(2-oxo)propanoate, 3-aminocrotonitrile, and 2-(trifluoromethyl)benzaldehyde produced a bright yellow solid. Yield 24%, mp 193-194. IR: 2982, 2845, 2202, 1745, 1627, 1601 cm$^{-1}$; NMR (200 MHz, CDCl$_3$)δ12.77 (s, 1H), 8.03 (d of d, J=7.7, 1.2 Hz, 1H), 7.70 (d of d, J=7.5, 1.2 Hz, 1H), 7.49–7.32 (m, 4H), 7.16 (t, J=6.8 Hz, 1H), 4.70 (s, 1H), 4.21–4.19 (m, 2H), 3.86 (s, 1H), 2.79–2.37 (m, 4H), 2.36 (s, 3H), 1.29 (t, J=7.2 Hz, 3H); MS m/z (int): 480 (16) [MI], 451 (1.4), 407 (100), 335 (12.2), 261 (24.3), 115 (12.7).

| Microanalysis: | C | H | N | F |
|---|---|---|---|---|
| Calculated | 67.49 | 4.83 | 5.83 | 11.86 |
| Found | 67.59 | 5.00 | 5.69 | 12.08 |

EXAMPLE 12 trans-Diethyl-2-(3,4-dihydro-3-oxo-2-(1H)-naphthalenylidene)-1,4-dihydro-6-methyl-4-[2(trifluoromethyl)phenyl]-3,5-pyridinedicarboxylate.

As for Example 1, ethyl 1,2,3,4-tetrahydro-1-oxonaphthalene-2-(2-oxo)propanoate, ethyl 3-aminocrotonate, and 2-(trifluoromethyl)benzaldehyde produced an orange glass. Yield 3%. IR (CHCl$_{13}$): 1735, 1695, 1622 cm$^{-1}$NMR (200 MHz, CDCl$_3$)δ12.70 (s, 1H), 8.02 (d of d, J=7.6, 1.4 Hz, 1H), 7.66 (d, J=7.5 Hz, 1H), 7.46–7.25 (m, 4H), 7.13 (t, J=7.3 Hz, 2H), 5.15 (s, 1H), 4.29–3.94 (m, 4H), 3.88 (s, 1H), 2.77–2.54 (m, 6H), 2.40–2.27 (m, 1H), 1.25 (t, J=7.2 Hz, 3H), 1.09 (t, J=7.2 Hz, 3H); MS m/z (int): 527 (34.4) [MI], 498 (2.4), 482 (8.0), 454 (100), 382 (34.6), 308 (15.8), 280 (12.8).

| Microanalysis: | C | H | N | F |
|---|---|---|---|---|
| Calculated | 66.03 | 5.35 | 2.66 | 10.80 |
| Found | 66.27 | 5.59 | 2.42 | 10.57 |

EXAMPLE 13

(2Z,3α,4β)-(±)-Diethyl-1,2,3,4-tetrahydro-6-methyl-2-[2-oxo-2-phenylethylidene]-4-[2-nitrophenyl-3,5-pyridinedicarboxylate.

Using a procedure analogous to that of Example 1, ethyl 5-phenyl-3,5-dioxopentanoate, 2-nitrobenzaldehyde, and ethyl 3-aminocrotonate produces the title product; mp glass. IR: 1738, 1702, 1622 cm$^{-1}$; NMR (200 MHz, CDCl$_3$)δ11.56 (s, 1H), 7.69 (d, J=7.6 Hz, 1H), 7.45–7.27 (m, 5H), 7.14 (d, J=7.6 Hz, 2H), 5.59 (s, 1H), 5.06 (s, 1H), 4.24 (m, 2H), 4.04 (m, 2H), 3.35 (s, 1H), 2.61 (s, 3H), 1.27 (t, J=7.1 Hz, 3H), 1.09 (t, J=7.1 Hz, 3H). MS Calcd: 535.13745; Found: 535.13776.

| Microanalysis: | C | H | N | Cl |
|---|---|---|---|---|
| Calculated | 60.51 | 4.70 | 2.61 | 6.62 |
| Found | 60.72 | 4.78 | 2.18 | 7.05 |

EXAMPLE 14

(2Z,3α,4β)-(±)-Diethyl-1,2,3,4-tetrahydro-6-methyl-2-[2-oxo-2-phenylethylidene]-4-[3-nitrophenyl]-3,5-pyridinedicarboxylate.

Using a procedure as for Example 1, ethyl 5-phenyl-3,5-dioxopentanoate, 3-nitrobenzaldehyde, and ethyl 3-aminocrotonate produces the title product; mp 93–94° C. IR: 2981, 1732, 1686, 1617 cm$^{-1}$; NMR (200 MHz, CDCl$_3$)δ11.94 (s, 1H), 7.89–7.64 (m, 2H), 7.50–7.35 (m, 3H), 7.35–7.11 (m, 5H), 5.90 (s, 1H), 4.56 (s, 1H), 4.23 (q, J=7.2 Hz, 2H), 4.10 (q, J=7.2 Hz, 2H), 3.48 (s, 1H), 2.56 (s, 3H), 1.26 (t, J=7.2 Hz, 3H), 1.18 (s, J=7.2 Hz, 3H).

| Microanalysis: | C | H | N |
|---|---|---|---|
| Calculated | 72.04 | 6.28 | 3.23 |
| Found | 71.75 | 6.24 | 3.23 |

EXAMPLE 15

(2Z,3α,4β)-(±)-Diethyl-1,2,3,4-tetrahydro-6-methyl-2-[2-oxo-2-phenylethylidene]-4-2,3-dichlorophenyl]-3,5-pyridinedicarboxylate.

Using a procedure as for Example 1, ethyl 5-phenyl-3,5-dioxopentanoate, 2,3-dichlorobenzaldehyde, and ethyl 3-aminocrotonate produces the title product; mp 135°–6° C. MS m/z (int): 502 (70.2) [M+], 456 (100), 427 (42).

| Microanalysis: | C | H | N | F |
|---|---|---|---|---|
| Calculated | 62.16 | 5.02 | 2.79 | 14.11 |
| Found | 62.06 | 5.00 | 2.69 | 14.15 |

EXAMPLE 16

(2Z,3α,4β)-(±)-Diethyl-1,2,3,4-tetrahydro-6-methyl-2-[2-oxo-2-phenylethylidene]-4-[2-pyridyl]-3,5-pyridinedicarboxylate.

Using a procedure as for Example 1, ethyl 5-phenyl-3,5-dioxopentanoate, 2-pyridinecarboxaldehyde, and ethyl 3-aminocrotonate produces the title product; mp 137° C. MS m/z (int): 479 (98) [M+1], 433 (100), 405 (32), 389 (23).

| Microanalysis: | C | H | N |
|---|---|---|---|
| Calculated | 65.26 | 5.48 | 5.85 |
| Found | 65.44 | 5.50 | 2.65 |

EXAMPLE 17

(2Z,3α,4β)-(±)-Diisopropyl-1,2,3,4-tetrahydro-6-methyl-2-[2-oxo-2-phenylethylidene]-4-[2-trifluoroethylphenyl]3,5-pyridinedicarboxylate.

Using a procedure as for Example 1, isopropyl 5-phenyl-3,5-dioxopentanoate, 2-trifluoromethylbenzaldehyde, and isopropyl 3-aminocrotonate produces the title product.

We claim:

1. A compound of the formula (I)

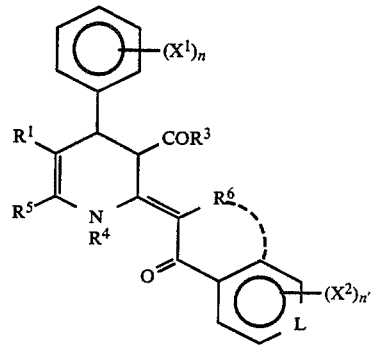

and pharmaceutically acceptable base or acid addition salts thereof; wherein (2) R$^1$ is
  (i) cyano,
  (ii) nitro,
  (iii)

wherein R$^2$ is (i) OR$^7$ wherein R$^7$ is hydrogen or (ii) ZR$^8$ wherein Z is alkylenyl of from one to six carbons, inclusive, and R$^8$ is hydrogen, optionally substituted phenyl which may have one or two substituents the same or different wherein the substituents are alkyl of from one to six carbons, inclusive, NO$_2$, halogen, alkoxy, amino, monoalkylamino wherein the alkyl is of from one to six carbons, inclusive, or dialkylamino wherein the alkyl is of from one to six carbons, inclusive; thienyl, furyl, pyryl, pyridyl, quinolyl, isoquinolyl, pyrimidyl, pyridazinyl, quinazolyl, quinoxalyl, pyrazolyl, imidazolyl, oxazolyl, isoxazolyl, thiazolyl, triazolyl, pyrazinyl, oxazinyl, thiazinyl, indolizinyl, indolyl, benzofuranyl, indazolyl, benzothienyl, benzimidazolyl, benzoxazolyl, cinnolinyl, phthalazinyl, naphthyridinyl or benzothiazinyl, amino, monoalkylamino wherein the alkyl is of from one to six carbons, inclusive, or dialkylamino wherein alkyl is of from one to six carbons, inclusive; or (iv) A-(CH$_2$)$_q$ wherein q is an integer of two, three, or four and A is

when taken together with R (3) R³ is
  (i) ZR⁸ wherein Z and R⁸ are each independently as defined above,
  (ii) OR⁷ wherein R⁷ is independently as defined above, or
  (iii) phenyl unsubstituted or substituted by from one to five, wherein the substituents are the same or different and are (i) hydrogen, (ii) alkyl of from one to six carbons, inclusive, (iii) nitro, (iv) alkoxy of from one to six carbons, inclusive, (v) cyano, (vi) amino, (vii) monoalkylamino wherein the alkyl is of from one to six carbons, inclusive, (viii) dialkylamino wherein the alkyl is of from one to six carbons, inclusive (ix) halogen or (x) trifluoromethyl;
(4) R⁴ is hydrogen or alkyl of from one to six carbons, inclusive
(5) R⁵ is (i) hydrogen,
  (ii) alkyl of from one to six carbons, inclusive, or
  (iii) taken together with R¹ as defined above;
(6) R⁶ is
  (i) hydrogen,
  (ii) alkyl of from one to six carbons, inclusive, or
  (iii) (CH₂)q, when taken together with X² when X² is on the carbon having the ---- and q' is 1, 2, or 3;
(7) n is an integer of zero through five;
(8) X¹ may each be the same or different and is
  (i) alkyl of from one to six carbons, inclusive,
  (ii) nitro,
  (iii) halogen,
  (iv) alkoxy of from one to six carbons, inclusive,
  (v) cyano,
  (vi) amino,
  (vii) monalkylamino wherein the alkyl is of from one to six carbons, inclusive,
  (viii) dialkylamino wherein the alkyl is of from one to six carbons, inclusive, or
  (ix) trifluoromethyl; and
(9) X² may each be the same or different and is
  (i) alkyl of from one to six atom carbons, inclusive,
  (ii) nitro,
  (iii) halogen,
  (iv) alkoxy of from one to six carbons, inclusive,
  (v) cyano,
  (vi) amino,
  (vii) monoalkylamino wherein the alkyl is of from one to six carbons, inclusive,
  (viii) dialkylamino wherein the alkyl is of from one to six, inclusive, or
  (ix) trifluoromethyl;
(10) n' is an integer of from zero through five;
(11) L is CH; or N with the proviso that then n' is 0 and --- is nothing.

2. A compound of claim 1 wherein R¹ is COOR².

3. A compound of claim 2 and being (2Z,3α,4β)-(±)diethyl-1,2,3,4-tetrahydro-6-methyl-2-(2-oxo-2-phenylethylidene)-4-[2-(trifluoromethyl)phenyl]-3,5-pyridinedicarboxylate.

4. A compound of claim 2 and being (2Z, 3α,4β)-(±)-diethyl-1,2,3,4-tetrahydro-6-methyl-2-[2-oxo-2-(4-pyridinyl)ethylidene]-4-[2-(trifluoromethyl) phenyl]-3,5-pyridinedicarboxylate.

5. A compound of claim 2 and being (2Z, 3α,4β)-diethyl-2-[2-(4-chlorophenyl)-2-oxoethylidene]-1,2,3,4-tetrahydro-6-methyl-4-[2-(trifluoromethyl) phenyl]-3,5-pyridinedicarboxylate.

6. A compound of claim 2 and being (2Z, 3α,4β)-diethyl-2-[2-(4-fluorophenyl)-2-oxoethylidene]-1,2,3,4-tetrahydro-6-methyl-4-[2-(trifluoromethyl) phenyl]-3,5-pyridinedicarboxylate.

7. A compound of claim 2 and being (2Z, 3α,4β)-diethyl-2-[2-(4-methylphenyl)-2-oxoethylidene]-1,2,3,4-tetrahydro-6-methyl-4-[2-(trifluoromethyl) phenyl]-3,5-pyridinedicarboxylate.

8. A compound of claim 2 and being (2Z, 3α,4β)-(±)-diethyl-1,2,3,4-tetrahydro-6-methyl-2-[2-oxo-2-(4-(dimethylamino)phenyl)ethylidene]-4-[2-(trifluoromethyl) phenyl]-3,5-pyridinedicarboxylate.

9. A compound of claim 2 and being (2Z, 3α,4β)-(±)-1,2,3,4-tetrahydro-6-methyl-5-nitro-2-[2-oxo-2-phenylethylidene]-4-[2-(trifluoromethyl)phenyl)]-3-pyridinedicarboxylic acid ethyl ester.

10. A compound of claim 2 and being [trans-(Z)]-2-[3-benzoyl-3,4-dihydro-6-methyl-5-nitro-4-[2-(trifluoromethyl) phenyl]-2-(1H)-pyridinylidene]-1-phenylethanone.

11. A compound of claim 2 and being (4α, 5β, 6Z)-(±)-ethyl-5-benzoyl-1,4,5,6-tetrahydro-2-methyl-6-(2-oxo-2-phenylethylidene)-4-[2-trifluoromethyl) phenyl]-3-pyridinecarboxylate.

12. A compound of claim 2 and being (2Z, 3α,4β)-ethyl-1,2,3,4,5,6,7,8-octahydro-5-oxo-2-(2-oxo-2-phenylethylidene)-4-[2-trifluoromethyl)phenyl]-3-quinolinecarboxylate.

13. A compound of claim 2 and being (2Z, 3α, 4β)-ethyl-5-cyano-2-(3,4-dihydro-1-oxo-2-(1H)-naphthalenylidene)-1,2,34-tetrahydro-6-methyl-4-[2-trifluoromethyl)phenyl]-3-pyridinecarboxylate.

14. A compound of claim 2 and being trans-diethyl-2-(3,4-dihydro-3-oxo-2-(1H)-naphthalenylidene)-1,4-dihydro-6-methyl-4-[2-(trifluoromethyl)phenyl]-3,5-pyridinedicarboxylate.

15. A compound of claim 2 which is (2Z, 3α, 4β)-(±)-**diethyl-1,2,3,4-tetrahydro-6-methyl-2-[2-oxo-2-(2-chlorophenyl) ethylidene]-4-[2-(trifluoromethyl) phenyl]-3,5-pyridinedicarboxylate.

16. A compound of claim 2 which is (2Z, 3α, 4β)-(±)-diethyl-2-[2-phenyl-2-oxoethylidene]-1,2,3,4-tetrahydro-6-methyl-4-phenyl-3,5-pyridinedicarboxylate.

17. A compound of claim 2 which is (2Z, 3α, 4β)-(±)-diethyl-4-(2,3-dichlorophenyl)-1,2,3,4-tetrahydro-6-methyl--2-[2-phenyl-2-oxoethylidene]-3,5-pyridinedicarboxylate.

18. A compound of claim 2 which is (2Z, 3α, 4β)-(±)-diethyl-4-(2-nitrophenyl)-1,2,3,4-tetrahydro-6-methyl-2-[2-phenyl-2-oxoethylidene]-3,5-pyridinedicarboxylate.

19. A pharmaceutical composition for the treatment of congestive heart failure, coronary heart disease, myocardial ischemia, angina, and hypertension comprising an anticongestive heart failure, cardiotonic, antimyocardial ischemic, antiangina, or antihypertensive effective amount of a compound as claimed in claim 1 together with a pharmaceutically acceptable carrier.

20. A method for treating congestive heart failure, coronary heart disease, myocardial ischemia, angina, and hypertension in a mammal suffering therefrom which comprises administering to such mammals a compound as claimed in claim 1 in unit dosage form.

* * * * *